US008968869B2

(12) United States Patent
Yang et al.

(10) Patent No.: US 8,968,869 B2
(45) Date of Patent: Mar. 3, 2015

(54) CURABLE-ON-DEMAND POLYSILOXANE COATING COMPOSITION

(75) Inventors: Yu Yang, Eden Prairie, MN (US); Michael A. Semonick, White Bear Lake, MN (US); George G. I. Moore, Afton, MN (US); Larry D. Boardman, Woodbury, MN (US); Michele A. Craton, Cottage Grove, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/807,344

(22) PCT Filed: Jun. 27, 2011

(86) PCT No.: PCT/US2011/042006
§ 371 (c)(1),
(2), (4) Date: Dec. 28, 2012

(87) PCT Pub. No.: WO2012/003153
PCT Pub. Date: Jan. 5, 2012

(65) Prior Publication Data
US 2013/0101841 A1    Apr. 25, 2013

Related U.S. Application Data

(60) Provisional application No. 61/360,007, filed on Jun. 30, 2010, provisional application No. 61/360,068, filed on Jun. 30, 2010.

(51) Int. Cl.
| C08G 77/12 | (2006.01) |
| C09D 183/06 | (2006.01) |
| C09J 7/02 | (2006.01) |
| C08L 83/06 | (2006.01) |
| C07F 9/06 | (2006.01) |
| C07F 9/572 | (2006.01) |
| C07F 9/6584 | (2006.01) |
| C08L 83/04 | (2006.01) |
| C09D 183/04 | (2006.01) |
| C09J 183/04 | (2006.01) |
| C08G 77/16 | (2006.01) |
| C08K 5/5399 | (2006.01) |

(52) U.S. Cl.
CPC .............. C08L 83/06 (2013.01); C07F 9/065 (2013.01); C07F 9/5721 (2013.01); C07F 9/6584 (2013.01); C07F 9/65846 (2013.01); C08L 83/04 (2013.01); C09D 183/04 (2013.01); C09J 183/04 (2013.01); C09D 183/06 (2013.01); C09J 7/0207 (2013.01); C08G 77/12 (2013.01); C08G 77/16 (2013.01); C08K 5/5399 (2013.01)
USPC ............ 428/345; 524/588; 522/148; 427/487

(58) Field of Classification Search
CPC ............................. C09D 183/06; C09J 7/0207
See application file for complete search history.

(56) References Cited

U.S. PATENT DOCUMENTS

| 2,708,289 A | 5/1955 | Collings |
| 3,328,482 A | 6/1967 | Northrup et al. |
| 3,445,417 A | 5/1969 | Layne et al. |
| 3,628,996 A | 12/1971 | Weber |
| 3,969,543 A | 7/1976 | Roberts et al. |
| 4,181,752 A | 1/1980 | Martens et al. |
| 4,269,963 A | 5/1981 | Homan et al. |
| 4,489,199 A * | 12/1984 | Wengrovius .................... 528/16 |
| 4,761,443 A | 8/1988 | Lopes |
| 5,219,958 A | 6/1993 | Noomen et al. |
| 5,286,815 A | 2/1994 | Leir et al. |
| 5,371,162 A | 12/1994 | Konings et al. |
| 5,403,909 A | 4/1995 | Rubinsztajn |
| 5,688,888 A | 11/1997 | Burkus, II et al. |
| 5,789,460 A * | 8/1998 | Harkness et al. ............. 522/148 |
| 5,820,944 A * | 10/1998 | Harkness et al. ............. 427/510 |
| 5,866,222 A | 2/1999 | Seth et al. |
| 5,891,529 A * | 4/1999 | Harkness et al. ............. 427/510 |
| 6,096,483 A * | 8/2000 | Harkness et al. ............. 430/325 |
| 6,124,371 A | 9/2000 | Stanssens et al. |
| 6,136,996 A | 10/2000 | Rubinsztajn et al. |

(Continued)

FOREIGN PATENT DOCUMENTS

| EP | 0 444 633 A2 | 9/1991 |
| JP | 61022094 A | 1/1986 |

(Continued)

OTHER PUBLICATIONS

Chemtob et al. "UV-Activated Silicone Oligomer Cross-Linking Through Photoacid and Photobase Organocatalyts", J. Appl. Polym. Sci. 2013, 6 pages.*
Suyama et al. "Photobase generators: Recent progress and application trend in polymer systems" Progress in Polymer Science, 34, 2009, 194-209.*
Org. Lett. 9, No. 1, pp. 1-169 (2007).
E. Lukevics and M. Dzintara, "Silylation of Hydroxyl-Containing Compounds with Aryl and Heteroaryl-Hydrosilanes in the Presence of Amines," Journal of Organometallic Chemistry 271, pp. 307-317 (1984).

(Continued)

Primary Examiner — Robert S Loewe
(74) Attorney, Agent, or Firm — Lucy C. Weiss

(57) ABSTRACT

A curable composition comprises (a) at least one polydiorganosiloxane, fluorinated polydiorganosiloxane, or combination thereof comprising reactive silane functionality comprising at least two hydroxysilyl moieties; (b) at least one polydiorganosiloxane, fluorinated polydiorganosiloxane, or combination thereof comprising reactive silane functionality comprising at least two hydrosilyl moieties; and (c) at least one photoactivatable composition that, upon exposure to radiation, generates at least one base selected from amidines, guanidines, phosphazenes, proazaphosphatranes, and combinations thereof; wherein at least one of the components (a) and (b) has an average reactive silane functionality of at least three.

20 Claims, No Drawings

(56) References Cited

U.S. PATENT DOCUMENTS

| | | | |
|---|---|---|---|
| 6,166,207 A | 12/2000 | Friedrich et al. | |
| 6,204,350 B1 | 3/2001 | Liu et al. | |
| 6,235,832 B1 | 5/2001 | Deng et al. | |
| 6,277,986 B1 | 8/2001 | Hall-Goulle et al. | |
| 6,551,761 B1 | 4/2003 | Hall-Goulle et al. | |
| 6,777,512 B1 * | 8/2004 | Sonnenschein et al. | 526/196 |
| 6,780,484 B2 | 8/2004 | Kobe et al. | |
| 6,805,933 B2 | 10/2004 | Patel et al. | |
| 6,835,422 B2 | 12/2004 | Kobe et al. | |
| 7,064,173 B2 | 6/2006 | Rubinsztajn et al. | |
| 7,148,370 B1 | 12/2006 | Rubinsztajn et al. | |
| 7,300,747 B2 * | 11/2007 | Okazaki et al. | 430/311 |
| 7,332,541 B2 | 2/2008 | Schindler et al. | |
| 7,482,391 B1 | 1/2009 | Cross et al. | |
| 7,538,104 B2 | 5/2009 | Baudin et al. | |
| 2001/0037008 A1 | 11/2001 | Sherman et al. | |
| 2004/0242867 A1 | 12/2004 | Baudin et al. | |
| 2006/0014844 A1 | 1/2006 | Lim et al. | |
| 2006/0111505 A1 | 5/2006 | Schindler et al. | |
| 2009/0171025 A1 | 7/2009 | Matsushita et al. | |
| 2010/0036049 A1 | 2/2010 | Matsushita et al. | |
| 2010/0041810 A1 | 2/2010 | Wakabayashi et al. | |
| 2011/0028585 A1 * | 2/2011 | Shiraishi et al. | 522/63 |
| 2011/0098392 A1 | 4/2011 | Barrandon et al. | |
| 2013/0101840 A1 | 4/2013 | Yang et al. | |
| 2013/0101841 A1 | 4/2013 | Yang et al. | |
| 2013/0102728 A1 | 4/2013 | Yang et al. | |

FOREIGN PATENT DOCUMENTS

| | | | |
|---|---|---|---|
| WO | WO2004/022618 A1 | 3/2004 | |
| WO | WO2007/149422 A2 | 12/2007 | |
| WO | WO 2009122664 A1 * | 10/2009 | C07D 335/16 |
| WO | WO 2010/146254 A1 | 12/2010 | |
| WO | WO 2010/149869 A1 | 12/2010 | |
| WO | WO 2012/003152 A1 | 1/2012 | |

OTHER PUBLICATIONS

Kanji et al., "Quaternary Ammonium Salt as DBU-Generating Photobase Generator", Journal of Photopolymer Science and Technology, 19(1), 81-84 (Jan. 1, 2006).

International Search Report for PCT Application No. PCT/US2011/042006, filed Jun. 27, 2011, 4 pp.

* cited by examiner

CURABLE-ON-DEMAND POLYSILOXANE COATING COMPOSITION

STATEMENT OF PRIORITY

This application claims the priorities of U.S. Provisional Applications Nos. 61/360,068, filed Jun. 30, 2010; and 61/360,007, also filed Jun. 30, 2010; the contents of which are hereby incorporated by reference.

FIELD

This invention relates to curable coating compositions comprising reactive silane functionality and, in other aspects, to processes for coating the compositions and articles prepared thereby.

BACKGROUND

Moisture-curable polysiloxane compositions cure in the presence of moisture to form crosslinked materials such as release coatings and surface treatments that are useful in many industries. For example, a polysiloxane or fluorinated polysiloxane is often selected to provide moisture-curable release coatings suitable for use with pressure-sensitive adhesives. The moisture for curing is typically obtained from the atmosphere or from a substrate to which the composition has been applied, although it can also be added to the composition (for example, to enable curing in depth or in confinement).

Moisture-curable polysiloxane compositions usually comprise siloxane polymers having groups (for example, alkoxysilyl or acyloxysilyl moieties) that can react in the presence of moisture to form cured (that is, crosslinked) materials. Moisture-curable compositions comprising alkoxysilyl or acyloxysilyl functionality typically cure in two reactions. In the first reaction, the alkoxysilyl or acyloxysilyl groups hydrolyze in the presence of moisture and a catalyst to form silanol compounds having hydroxysilyl groups. In the second reaction, the hydroxysilyl groups condense with other hydroxysilyl, alkoxysilyl, or acyloxysilyl groups in the presence of a catalyst to form —Si—O—Si— linkages. The two reactions occur essentially simultaneously upon generation of the silanol compound. Commonly used catalysts for the two reactions include Bronsted and Lewis acids. A single material can catalyze both reactions.

Preferably, the hydrolysis and condensation reactions proceed quickly after the moisture-curable composition has been applied, for example, to a substrate. At the same time, however, the reactions must not occur prematurely, for example, during processing or storage.

A good balance between these properties is often difficult to obtain, as rapid reactivity and storage stability are opposite properties to each other. For example, highly active catalysts such as tetraalkyl titanate esters rapidly accelerate the moisture-curing reaction but, at the same time, can make it difficult to process the materials without risking premature gelation in feed tanks, coating equipment, and other manufacturing and handling apparatus. Control of the amount of moisture can be critical, with too little moisture potentially resulting in slow or incomplete cure and too much moisture resulting in premature cure.

A variety of approaches have been used for providing moisture-curable compositions that have acceptable cure rates without processing and storage difficulties. For example, two-part systems have been developed (one part comprising a functional siloxane polymer and the other part comprising a catalyst), with the two parts being mixed immediately prior to use. While this approach has been useful in small-scale applications, it has been less efficient for large-scale manufacturing, where delays caused by having to mix the two parts have been undesirable. Furthermore, coating operations must be completed expeditiously before the composition cures in the pot, and this has been difficult when working with large surface area substrates or a large volume of composition.

Ammonium salt catalysts have been developed that are inactive until heated sufficiently to liberate an acid compound that initiates the moisture curing reaction. Liberation of the acid also generates an amine, however, that must be removed by evaporation. In addition, the heat used to activate the catalyst can damage heat-sensitive substrates onto which the composition has been applied.

Other materials (for example, onium salts such as sulfonium and iodonium salts) have been used to generate acid species in situ upon irradiation (for example, irradiation with ultraviolet light). Such materials have not required heat activation and therefore have enabled the use of heat-sensitive substrates without damage (and without the production of undesirable species requiring removal), but the materials have been relatively expensive, have required moisture control, and have exhibited cure inhibition on some substrates.

Conventional tin catalysts such as dibutyl tin dilaurate can provide stable curable polysiloxane compositions that can be processed and coated without premature gelation. In addition to typical moisture-curable systems, it has been found that curable compositions comprising dual reactive silane functionality in the form of hydrosilyl and hydroxysilyl groups (dehydrogenatively-curable systems) can be cured by using tin catalysts. The compositions have been widely used for pressure-sensitive adhesive and mold release applications but have sometimes suffered from relatively short pot lives. In addition, the use of tin catalysts is becoming particularly problematic because the organotin compounds generally employed as catalysts are now considered to be toxicologically objectionable.

Acceleration of cure has been achieved by the use of compounds such as substituted guanidines, diorganosulfoxides, imidazoles, amidines, and amines in combination with tin catalysts in room temperature vulcanizing silicone compositions. Amine compounds including amidines have also been proposed for use in the absence of tin catalysts for curing moisture-curable, silyl-functional organic polymers, but practical curability of alkoxysilyl-functional organic polymers and acceptable adhesion to substrates were achieved only with strongly basic amines (those exhibiting a pH of at least 13.4 in aqueous solution).

SUMMARY

Thus, we recognize that there exists an ongoing need for curable polysiloxane compositions that can provide acceptable cure rates without significant processing and storage difficulties (for example, due to premature gelation). Preferably, these compositions will be efficiently processable (for example, without the need for mixing of a two-part system prior to cure), will employ catalysts that do not generate species requiring removal, and/or will not require heat activation (so as to enable curing at relatively low temperatures and/or the use of heat-sensitive substrates). The compositions preferably will employ catalysts that are relatively non-toxic, provide compositions that are relatively stable in solution but relatively fast-curing upon drying, effective in relatively low concentrations, and/or effective under relatively low (or no) moisture conditions. Ideally, the compositions will be curable on demand (for example, by generation of the catalyst in situ) and coatable without the need for significant addition of solvent (for example, in 100 percent solids form).

Briefly, in one aspect, this invention provides a curable polysiloxane composition comprising dual reactive silane functionality. The composition comprises (a) at least one polydiorganosiloxane, fluorinated polydiorganosiloxane, or combination thereof comprising reactive silane functionality comprising at least two hydroxysilyl moieties (that is, monovalent moieties comprising a hydroxyl group bonded directly to a silicon atom);

(b) at least one polydiorganosiloxane, fluorinated polydiorganosiloxane, or combination thereof comprising reactive silane functionality comprising at least two hydrosilyl moieties (that is, monovalent moieties comprising a hydrogen atom bonded directly to a silicon atom); and (c) at least one photoactivatable composition that, upon exposure to radiation, generates at least one base selected from amidines, guanidines, phosphazenes, proazaphosphatranes, and combinations thereof;

wherein at least one of components (a) and (b) has an average reactive silane functionality of at least three (that is, component (a) has at least three hydroxysilyl moieties (on average), component (b) has at least three hydrosilyl moieties (on average), or both). Components (a) and (b) preferably comprise at least one polydiorganosiloxane (more preferably, at least one polydialkylsiloxane; most preferably, at least one polydimethylsiloxane). Preferably, component (a) is hydroxyl-end-blocked, so as to comprise two terminal hydroxysilyl moieties (on average).

The photoactivatable composition preferably comprises at least one 1,3-diamine compound that is substituted on at least one nitrogen atom by at least one aralkyl radical. The base that is generated upon exposure of the photoactivatable composition to radiation preferably comprises at least one amidine (most preferably, 1,8-diazabicyclo[5.4.0]-7-undecene (DBU)).

It has been discovered that, unlike standard amine bases such as 4,4'-trimethylenebis(1-methylpiperidine) (which are ineffective), the above-described bases can effectively catalyze the curing (apparently, by condensation) of polysiloxane compositions comprising reactive silane functionality in the form of hydrosilyl and hydroxysilyl moieties. It has been further discovered that photoactivatable compositions can be effectively used to generate the bases in situ. This in situ generation has been found to provide curable-on-demand polysiloxane compositions that can exhibit enhanced storage stability and/or pot life and that can be coated in completely solvent-free (that is, 100 percent solids) or substantially solvent-free (using only a relatively small amount of solvent) form.

Upon photoactivation, the curable polysiloxane compositions can cure relatively rapidly (for example, upon irradiation curing can occur within periods of time as short as seconds or less) even at temperatures as low as ambient (for example, about 23° C.), without the need for heat activation, and the photoactivatable compositions can be effective in relatively small amounts (for example, at concentrations as low as about 0.5 weight percent or less, based upon the total weight of components (a), (b), and (c)). Thus, curable polysiloxane compositions comprising the photoactivatable compositions can be suitable for use in high speed coating and curing operations in an industrial setting, without the need for addition of heat. In spite of such effective curability, the curable polysiloxane compositions can exhibit relatively good storage stability (for example, for a period of weeks or more in a closed container) and/or relatively long pot life (for example, on the order of days in the absence of light) in 100 percent solids form or, optionally, in a variety of solvents (for example, heptane, methyl ethyl ketone, or a combination thereof), without the need for mixing of a two-part system immediately prior to use.

In surprising contrast with prior art compositions, the in situ-generated bases can be effective in the curable polysiloxane composition of the invention in the substantial absence of other condensation catalysts and/or in the substantial absence of moisture. The bases can be used as substitutes for conventional tin catalysts to provide organometallic catalyst-free, curable polysiloxane compositions, without the need for changes in the nature of the polysiloxane components of conventional tin-cured polysiloxane compositions (for example, release coating compositions such as Syl-Off™ 292 coating composition, available from Dow Corning Corporation, Midland, Mich.). Unlike the conventional tin catalysts, at least some of the bases (for example, DBU) and their photoactivatable precursors are relatively non-toxic and therefore suitable for use in preparing relatively environmentally friendly or "green" polysiloxane compositions.

The curable polysiloxane composition of the invention can be cured to provide crosslinked networks having properties that can be tailored to the requirements of various different applications (for example, by varying the natures, relative amounts, and/or degrees of reactive silane functionality of starting components (a) and/or (b)). Thus, the curable polysiloxane composition can be used to provide coatings having a variety of surface properties for use in numerous coating applications (for example, use as release coatings for pressure-sensitive adhesives, protective coatings, water- and/or oil-repellent coatings or surface treatments, and the like). The curable polysiloxane composition of the invention can be particularly useful in relatively sensitive applications requiring careful and/or tailored control of surface properties (for example, release coating applications), as the base catalysts and their photoactivatable precursors do not appear to produce species requiring removal and, in some embodiments, are sufficiently volatile to be evaporated from the composition during processing, thereby leaving essentially no catalyst contamination in the cured material (in contrast with the metal contamination of conventional tin catalysts, which can be particularly problematic in the area of electronics).

In view of the foregoing, at least some embodiments of the curable polysiloxane composition of the invention meet the above-described, ongoing need for curable-on-demand, solvent-free compositions that can provide acceptable (or even exceptional) cure rates without significant processing and storage difficulties (for example, without the need for mixing of a two-part system prior to cure, for contaminant removal, and/or for heat activation). At least some embodiments of the curable polysiloxane composition also employ catalysts and catalyst precursors that are relatively non-toxic, while being effective in relatively low concentrations and/or under relatively low (or no) moisture conditions.

In another aspect, this invention also provides a coating process comprising (a) providing the above-described curable polysiloxane composition of the invention;

(b) providing at least one substrate having at least one major surface;

(c) applying the curable polysiloxane composition to at least a portion of at least one major surface of the substrate; and (d) inducing the curable polysiloxane composition to cure to form a coating by exposing at least a portion of the curable polysiloxane composition to radiation.

In yet another aspect, this invention provides an article comprising at least one substrate having at least one major surface, the substrate bearing, on at least a portion of at least one major surface, a coating prepared by the above-described coating process.

DETAILED DESCRIPTION

In the following detailed description, various sets of numerical ranges (for example, of the number of carbon atoms in a particular moiety, of the amount of a particular component, or the like) are described, and, within each set, any lower limit of a range can be paired with any upper limit of a range. Such numerical ranges also are meant to include all numbers subsumed within the range (for example, 1 to 5 includes 1, 1.5, 2, 2.75, 3, 3.80, 4, 5, and so forth).

As used herein, the term "and/or" means one or all of the listed elements or a combination of any two or more of the listed elements.

The words "preferred" and "preferably" refer to embodiments of the invention that may afford certain benefits under certain circumstances. Other embodiments may also be preferred, however, under the same or other circumstances. Furthermore, the recitation of one or more preferred embodiments does not imply that other embodiments are not useful, and is not intended to exclude other embodiments from the scope of the invention.

The term "comprises" and variations thereof do not have a limiting meaning where these terms appear in the description and claims.

As used herein, "a," "an," "the," "at least one," and "one or more" are used interchangeably.

The above "Summary of the Invention" section is not intended to describe every embodiment or every implementation of the invention. The detailed description that follows more particularly describes illustrative embodiments. Throughout the detailed description, guidance is provided through lists of examples, which examples can be used in various combinations. In each instance, a recited list serves only as a representative group and should not be interpreted as being an exclusive list.

Definitions

As used in this patent application:

"catenated heteroatom" means an atom other than carbon (for example, oxygen, nitrogen, or sulfur) that replaces one or more carbon atoms in a carbon chain (for example, so as to form a carbon-heteroatom-carbon chain or a carbon-heteroatom-heteroatom-carbon chain);

"cure" means conversion to a crosslinked polymer network (for example, through catalysis);

"fluoro-" (for example, in reference to a group or moiety, such as in the case of "fluoroalkylene" or "fluoroalkyl" or "fluorocarbon") or "fluorinated" means only partially fluorinated such that there is at least one carbon-bonded hydrogen atom;

"fluorochemical" means fluorinated or perfluorinated;

"heteroorganic" means an organic group or moiety (for example, an alkyl or alkylene group) containing at least one heteroatom (preferably, at least one catenated heteroatom);

"hydrosilyl" refers to a monovalent moiety or group comprising a silicon atom directly bonded to a hydrogen atom (for example, the hydrosilyl moiety can be of formula —Si(R)$_{3-p}$(H)$_p$, where p is an integer of 1, 2, or 3 and R is a hydrolyzable or non-hydrolyzable group (preferably, non-hydrolyzable) such as alkyl or aryl);

"hydroxysilyl" refers to a monovalent moiety or group comprising a silicon atom directly bonded to a hydroxyl group (for example, the hydroxysilyl moiety can be of formula —Si(R)$_{3-p}$(OH)$_p$ where p is an integer of 1, 2, or 3 and R is a hydrolyzable or non-hydrolyzable group (preferably, non-hydrolyzable) such as alkyl or aryl);

"isocyanato" means a monovalent group or moiety of formula —NCO;

"mercapto" means a monovalent group or moiety of formula —SH;

"oligomer" means a molecule that comprises at least two repeat units and that has a molecular weight less than its entanglement molecular weight; such a molecule, unlike a polymer, exhibits a significant change in properties upon the removal or addition of a single repeat unit;

"oxy" means a divalent group or moiety of formula —O—; and

"perfluoro-" (for example, in reference to a group or moiety, such as in the case of "perfluoroalkylene" or "perfluoroalkyl" or "perfluorocarbon") or "perfluorinated" means completely fluorinated such that, except as may be otherwise indicated, there are no carbon-bonded hydrogen atoms replaceable with fluorine.

Component (a)

Polysiloxanes suitable for use as component (a) of the curable polysiloxane composition of the invention include polydiorganosiloxanes, fluorinated polydiorganosiloxanes, and combinations thereof (preferably, polydiorganosiloxanes) comprising reactive silane functionality comprising at least two hydroxysilyl moieties (that is, monovalent moieties comprising a hydroxyl group bonded directly to a silicon atom). The polysiloxanes can be oligomers, polymers, or a combination thereof. Preferably, the polysiloxanes are polymers, which can be linear, branched, or cyclic. Useful polymers include those that have random, alternating, block, or graft structures, or a combination thereof.

The molecular weight and the reactive silane functionality of component (a) (including the number and nature of the hydroxysilyl moieties) of the polysiloxanes can vary widely, depending upon, for example, the molecular weight and the reactive silane functionality of component (b) and the properties desired for the curable and/or cured composition. At least one of components (a) and (b) has an average reactive silane functionality of at least three, however (that is, component (a) has at least three hydroxysilyl moieties (on average), component (b) has at least three hydrosilyl moieties (on average), or both), so as to enable the formation of a crosslinked network.

Preferably, the polydiorganosiloxanes, fluorinated polydiorganosiloxanes, and combinations thereof used for component (a) are hydroxyl-endblocked, so as to comprise two terminal hydroxysilyl moieties (on average). The polysiloxanes preferably have a weight average molecular weight of about 150 to about 1,000,000 (more preferably, about 1,000 to about 1,000,000).

A preferred class of useful polysiloxanes includes those that can be represented by the following general formula:

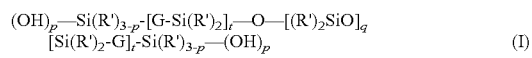
$$[Si(R')_2\text{-}G]_t\text{-}Si(R')_{3-p}\text{—}(OH)_p \quad (I)$$

wherein each p is independently an integer of 1, 2, or 3 (preferably, 1); each G is independently a divalent linking group; each R' is independently selected from alkyl, alkenyl, fluoroalkyl, aryl, fluoroaryl, cycloalkyl, fluorocycloalkyl, heteroalkyl, heterofluoroalkyl, heteroaryl, heterofluoroaryl, heterocycloalkyl, heterofluorocycloalkyl, and combinations thereof; q is an integer of 0 to about 15,000 (preferably, about 20 to about 15,000); and each t is independently an integer of 0 or 1 (preferably, 0). Preferably, each R' is independently selected from alkyl (preferably, having 1 to about 8 carbon atoms), fluoroalkyl (preferably, having 3 to about 8 carbon atoms; more preferably, $R_fC_2H_4—$, wherein $R_f$ is a fluorinated or perfluorinated alkyl group having 1 to about 6 carbon atoms (preferably, 1 to about 6 carbon atoms)), aryl, and combinations thereof. More preferably, each R' is independently selected from methyl, $C_4F_9C_2H_4—$, $C_6F_{13}C_2H_4—$, $CF_3C_2H_4—$, $C_6H_5C_2H_4—$, phenyl, and combinations thereof (even more preferably, methyl, $CF_3C_2H_4—$, phenyl, $C_4F_9C_2H_4—$, and combinations thereof; most preferably, methyl). Each divalent linking group, G, is preferably independently selected from oxy, alkylene, arylene, heteroalkylene, heteroarylene, cycloalkylene, heterocycloalkylene, and combinations thereof (more preferably, selected from oxy, alkylene, arylene, and combinations thereof). Heteroatoms (in G and/or R') can include oxygen, sulfur, nitrogen, phosphorus, and combinations thereof (preferably, oxygen, sulfur, and combinations thereof; more preferably, oxygen). G can contain fluorine, provided that it is separated from silicon by at least two carbon atoms.

Preferred polysiloxanes include hydroxyl-endblocked polydimethylsiloxane homopolymer, as well as hydroxyl-endblocked copolymers comprising dimethylsiloxane units and up to about 40 or 50 mole percent of other units selected from dialkylsiloxane units, (alkyl)(methyl)siloxane units, and (alkyl)(phenyl)siloxane units wherein each alkyl group is independently selected from alkyl groups having two to about 8 carbon atoms (for example, hexyl), di(fluoroalkyl)siloxane units, (fluoroalkyl)(methyl)siloxane units, and (fluoroalkyl)(phenyl)siloxane units wherein each fluoroalkyl group is independently selected from fluoroalkyl groups having 3 to about 8 carbon atoms (for example, trifluoropropyl or nonafluorohexyl), diphenylsiloxane units, and combinations thereof.

The polysiloxanes useful as component (a) can be used in the curable composition of the invention singly or in the form of mixtures of different polysiloxanes. Sometimes mixtures can be preferred. A preferred composition for use as component (a) comprises a mixture of (1) at least one polydiorganosiloxane, fluorinated polydiorganosiloxane, or combination thereof (preferably, at least one polydiorganosiloxane) having a weight average molecular weight in the range of about 300,000 to about 1,000,000 (more preferably, about 400,000 to about 900,000; most preferably, about 500,000 to about 700,000) and (2) at least one polydiorganosiloxane, fluorinated polydiorganosiloxane, or combination thereof (preferably, at least one polydiorganosiloxane) having a weight average molecular weight in the range of about 150 to about 150,000 (more preferably, about 10,000 to about 120,000; most preferably, about 10,000 to about 15,000). The relative amounts of component (1) and component (2) and their molecular weights can be selected for release applications according to the nature of the adhesive (or other material) to be utilized and the level of release desired.

For example, for mold release applications, the weight ratio of the former polysiloxane to the latter polysiloxane can range from about 3:1 to about 19:1 (preferably, about 4:1 to about 9:1; more preferably, about 6:1). For pressure sensitive adhesive (PSA) release applications, the weight ratio of the former polysiloxane to the latter polysiloxane can range, for example, from about 2:1 to about 1:10 (preferably, about 1:1 to about 1:6; more preferably, about 1:2 to about 1:4).

The polysiloxanes suitable for use as component (a) can be prepared by known synthetic methods and many are commercially available. For example, the hydroxysilyl-functional components of Syl-Off™ 292 coating composition (available from Dow Corning Corporation, Midland, Mich.) are preferred polysiloxanes, and other useful polysiloxanes of varying molecular weight can be obtained from Gelest, Inc., Morrisville, Pa. (see, for example, the polysiloxanes described in *Silicon Compounds: Silanes and Silicones*, Second Edition, edited by B. Arkles and G. Larson, Gelest, Inc. (2008)).

Component (b)

Polysiloxanes suitable for use as crosslinker component (b) of the curable composition of the invention include polydiorganosiloxanes, fluorinated polydiorganosiloxanes, and combinations thereof comprising reactive silane functionality comprising at least two hydrosilyl moieties (that is, monovalent moieties comprising a hydrogen atom bonded directly to a silicon atom). The polysiloxanes can be small molecules, oligomers, polymers, or a combination thereof. Preferably, the polysiloxanes are polymers. The polysiloxanes can be linear, branched, or cyclic. Useful polymers include those that have random, alternating, block, or graft structures, or a combination thereof.

The molecular weight and the reactive silane functionality of component (b) (including the number and nature of the hydrosilyl moieties) can vary widely, depending upon, for example, the molecular weight and the reactive silane functionality of component (a) and the properties desired for the curable and/or cured composition. Preferably, component (b) has an average reactive silane functionality of at least three (so as to enable the formation of a crosslinked network when component (a) is hydroxyl-endblocked). The polysiloxanes preferably have a weight average molecular weight of about 100 to about 100,000.

A preferred class of polysiloxanes includes those that can be represented by the following general formula:

$$R'_2R''SiO(R'_2SiO)_r(HR'SiO)_sSiR''R'_2 \qquad (II)$$

wherein R' is as defined above for Formula (I); each R" is independently hydrogen or R'; r is an integer of 0 to about 150 (preferably, 0 to about 100; more preferably, 0 to about 20); and s is an integer of 2 to about 150 (preferably, about 5 to about 100; more preferably, about 20 to about 80). Most preferably, both R" and R' are methyl, r is 0, and/or s is about 40.

Preferred hydride-functional polysiloxanes include those comprising polydimethylsiloxane homopolymer, as well as those comprising copolymer(s) comprising dimethylsiloxane units and up to about 40 or 50 mole percent of other units selected from dialkylsiloxane units, (alkyl)(methyl)siloxane units, and (alkyl)(phenyl)siloxane units wherein each alkyl group is independently selected from alkyl groups having two to about 8 carbon atoms (for example, hexyl), di(fluoroalkyl)siloxane units, (fluoroalkyl)(methyl)siloxane units, and (fluoroalkyl)(phenyl)siloxane units wherein each fluoroalkyl group is independently selected from fluoroalkyl groups having 3 to about 8 carbon atoms (for example, trifluoropropyl or nonafluorohexyl), diphenylsiloxane units, and combinations thereof. Although homopolymer is often preferred, copolymers can be preferred for some applications.

The polysiloxanes useful as component (b) can be used in the curable composition of the invention singly or in the form of mixtures of different polysiloxanes. The polysiloxanes can be prepared by known synthetic methods and many are commercially available. For example, Syl-Off™ Q2-7560 crosslinker, Syl-Off™ 7678 crosslinker, and the hydrosilyl-functional component (for example, Syl-Off™ 7048 crosslinker) of Syl-Off™ 292 and Syl-Off™ 294 coating compositions (all available from Dow Corning Corporation, Midland, Mich.) are preferred polysiloxanes, and other useful polysiloxane crosslinkers of varying molecular weight can be obtained from Gelest, Inc., Morrisville, Pa. (see, for example, the polysiloxanes described in *Silicon Compounds: Silanes and Silicones*, Second Edition, edited by B. Arkles and G. Larson, Gelest, Inc. (2008)).

Component (c)

Photoactivatable compositions suitable for use as component (c) of the curable composition of the invention include compositions (known or hereafter-developed compounds or mixtures) that, upon exposure to radiation (preferably, ultraviolet radiation, visible radiation, or a combination thereof), generate at least one base selected from amidines, guanidines (including substituted guanidines such as biguanides), phosphazenes, proazaphosphatranes (also known as Verkade's bases), and combinations thereof. Photoactivatable compositions that generate self-protonatable forms of the bases (for example, aminoacids such as arginine) generally are less suitable and therefore excluded, as such forms of the bases are self-neutralized. Preferred photoactivatable compositions include those that, upon exposure to radiation, generate at least one base selected from amidines, guanidines, and combinations thereof (more preferably, amidines and combinations thereof most preferably, cyclic amidines and combinations thereof).

It has been discovered that the bases of the listed structural classes can effectively catalyze reaction between components (a) and (b), as described above. The bases (and their photoactivatable precursors) can be used in the curable composition singly (individually) or in the form of mixtures (including different structural classes).

Useful photoactivatable compositions include those that, upon exposure to radiation, generate amidines that can be represented by the following general formula:

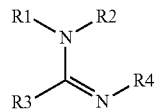

(III)

wherein R1, R2, R3, and R4 are each independently selected from hydrogen, monovalent organic groups, monovalent heteroorganic groups (for example, comprising nitrogen, oxygen, phosphorus, or sulfur in the form of groups or moieties that are bonded through a carbon atom and that do not contain acid functionality such as carboxylic or sulfonic), and combinations thereof; and wherein any two or more of R1, R2, R3, and R4 optionally can be bonded together to form a ring structure (preferably, a five-, six-, or seven-membered ring; more preferably, a six- or seven-membered ring). The organic and heteroorganic groups preferably have from 1 to about 20 carbon atoms (more preferably, from 1 to about 10 carbon atoms; most preferably, from 1 to about 6 carbon atoms). Preferably, R4 is not hydrogen.

Photoactivatable compositions that can generate amidines comprising at least one ring structure (that is, cyclic amidines) are generally preferred. Photoactivatable compositions that can generate cyclic amidines comprising two ring structures (that is, bicyclic amidines) are more preferred.

Representative examples of useful photoactivatable compositions include those that can generate amidine compounds such as 1,2-dimethyl-1,4,5,6-tetrahydropyrimidine, 1-ethyl-2-methyl-1,4,5,6-tetrahydropyrimidine, 1,2-diethyl-1,4,5,6-tetrahydropyrimidine, 1-n-propyl-2-methyl-1,4,5,6-tetrahydropyrimidine, 1-isopropyl-2-methyl-1,4,5,6-tetrahydropyrimidine, 1-ethyl-2-n-propyl-1,4,5,6-tetrahydropyrimidine, 1-ethyl-2-isopropyl-1,4,5,6-tetrahydropyrimidine, DBU (that is, 1,8-diazabicyclo[5.4.0]-7-undecene), DBN (that is, 1,5-diazabicyclo[4.3.0]-5-nonene), and the like, and combinations thereof. Preferred photoactivatable compositions include those that can generate amidines such as 1,2-dimethyl-1,4,5,6-tetrahydropyrimidine, DBU (that is, 1,8-diazabicyclo[5.4.0]-7-undecene), DBN (that is, 1,5-diazabicyclo[4.3.0]-5-nonene), and combinations thereof, with those that can generate DBU, DBN, and combinations thereof being more preferred and those that can generate DBU most preferred.

Useful photoactivatable compositions include those that, upon exposure to radiation, generate guanidines that can be represented by the following general formula:

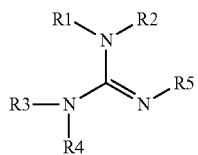

(IV)

wherein R1, R2, R3, R4, and R5 are each independently selected from hydrogen, monovalent organic groups, monovalent heteroorganic groups (for example, comprising nitrogen, oxygen, phosphorus, or sulfur in the form of groups or moieties that are bonded through a carbon atom and that do not contain acid functionality such as carboxylic or sulfonic), and combinations thereof; and wherein any two or more of R1, R2, R3, R4, and R5 optionally can be bonded together to form a ring structure (preferably, a five-, six-, or seven-membered ring; more preferably, a five- or six-membered ring; most preferably, a six-membered ring). The organic and heteroorganic groups preferably have from 1 to about 20 carbon atoms (more preferably, from 1 to about 10 carbon atoms; most preferably, from 1 to about 6 carbon atoms). Preferably, R5 is not hydrogen.

Photoactivatable compositions that can generate guanidines comprising at least one ring structure (that is, cyclic guanidines) are generally preferred. Photoactivatable compositions that can generate cyclic guanidines comprising two ring structures (that is, bicyclic guanidines) are more preferred.

Representative examples of useful photoactivatable compositions include those that can generate guanidine compounds such as 1-methylguanidine, 1-n-butylguanidine, 1,1-dimethylguanidine, 1,1-diethylguanidine, 1,1,2-trimethylguanidine, 1,2,3-trimethylguanidine, 1,3-diphenylguanidine, 1,1,2,3,3-pentamethylguanidine, 2-ethyl-1,1,3,3-tetramethylguanidine, 1,1,3,3-tetramethyl-2-n-propylguanidine, 1,1,3,3-tetramethyl-2-isopropylguanidine, 2-n-butyl-1,1,3,3-tetramethylguanidine, 2-tert-butyl-1,1,3,3-tetramethylguanidine, 1,2,3-tricyclohexylguanidine, TBD (that is, 1,5,7-triazabicyclo[4.4.0]dec-5-ene), MTBD (that is, 7-methyl-1,5,7-triazabicyclo[4.4.0]dec-5-ene), 7-ethyl-1,5,7-triazabicyclo[4.4.0]dec-5-ene, 7-n-propyl-1,5,7-triazabicyclo[4.4.0]dec-5-ene, 7-isopropyl-1,5,7-triazabicyclo[4.4.0]dec-5-ene, 7-n-butyl-1,5,7-triazabicyclo[4.4.0]dec-5-ene, 7-isobutyl-1,5,7-triazabicyclo[4.4.0]dec-5-ene, 7-tert-butyl-1,5,7-triazabicyclo[4.4.0]dec-5-ene, 7-cyclohexyl-1,5,7-triazabicyclo[4.4.0]dec-5-ene, 7-n-octyl-1,5,7-triazabicyclo[4.4.0]dec-5-ene, 7-2-ethylhexyl-1,5,7-triazabicyclo[4.4.0]dec-5-ene, 7-decyl-1,5,7-triazabicyclo[4.4.0]dec-5-ene, biguanide, 1-methylbiguanide, 1-n-butylbiguanide, 1-(2-ethylhexyl)biguanide, 1-n-octadecylbiguanide, 1,1-dimethylbiguanide, 1,1- diethylbiguanide, 1-cyclohexylbiguanide, 1-allylbiguanide, 1-n-butyl-N2-ethylbiguanide, 1,1'-ethylenebisguanide, 1-[3-(diethylamino)propyl]biguanide, 1-[3-(dibutylamino)propyl]biguanide, N',N"-dihexyl-3,12-diimino-2,4,11,13-tetraazatetradecanediamidine, and the like, and combinations thereof. Preferred photoactivatable compositions include those that can generate guanidines such as TBD (that is, 1,5,7-triazabicyclo[4.4.0]dec-5-ene), MTBD (that is, 7-methyl-1,5,7-triazabicyclo[4.4.0]dec-5-ene), 2-tert-butyl-1,1,3,3-tetramethylguanidine, and combinations thereof. More preferred photoactivatable compositions include those that can generate TBD, MTBD, and combinations thereof.

If desired, photoactivatable compositions that can generate amidines and/or guanidines exhibiting a pH value lower than 13.4 when measured according to JIS Z 8802 (for example, 1,3-diphenylguanidine, DBU, DBN, or a combination thereof; preferably, DBU, DBN, or a combination thereof) can be utilized. The referenced method for determining the pH of aqueous solutions, JIS Z 8802, is carried out by first preparing an aqueous solution of base by adding 5 millimoles of base to 100 g of a mixed solvent composed of isopropyl alcohol and water in a weight ratio of 10:3. The pH of the resulting solution is then measured at 23° C. using a pH meter (for example, a Horiba Seisakusho Model F-22 pH meter).

Useful photoactivatable compositions further include those that, upon exposure to radiation, generate phosphazenes that can be represented by the following general formula:

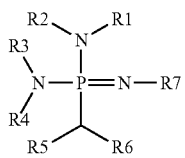

(V)

wherein R1, R2, R3, R4, R5, R6, and R7 are each independently selected from hydrogen, monovalent organic groups, monovalent heteroorganic groups (for example, comprising nitrogen, oxygen, phosphorus, or sulfur in the form of groups or moieties that are bonded through a carbon atom and that do not contain acid functionality such as carboxylic or sulfonic), and combinations thereof; and wherein any two or more of R1, R2, R3, R4, R5, R6, and R7 optionally can be bonded together to form a ring structure (preferably, a five-, six-, or seven-membered ring; more preferably, a five- or six-membered ring; most preferably, a six-membered ring). The organic and heteroorganic groups preferably have from 1 to about 20 carbon atoms (more preferably, from 1 to about 10 carbon atoms; most preferably, from 1 to about 6 carbon atoms). Preferably, R7 is not hydrogen.

Representative examples of useful photoactivatable compositions include those that can generate phosphazene compounds such as

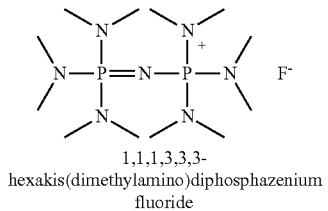

1,1,1,3,3,3-hexakis(dimethylamino)diphosphazenium fluoride

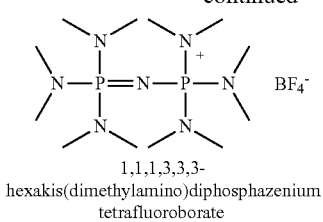

1,1,1,3,3,3-hexakis(dimethylamino)diphosphazenium tetrafluoroborate

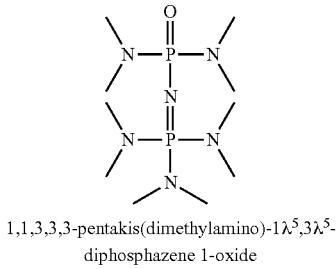

1,1,3,3,3-pentakis(dimethylamino)-1λ$^5$,3λ$^5$-diphosphazene 1-oxide

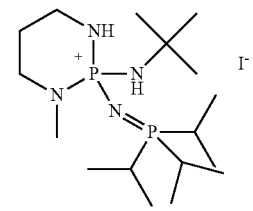

2-tert-butylamino-1-methyl-2-[tris(dimethylamino)phosphoranylidenamino]-perhydro-1,3,2-diazaphosphorinium iodide

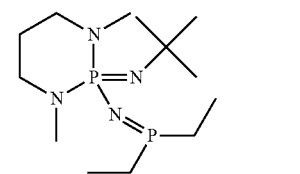

2-tert-butylamino-2-diethylamino-1,3-dimethylperhydro-1,3,2-diazaphosphorine

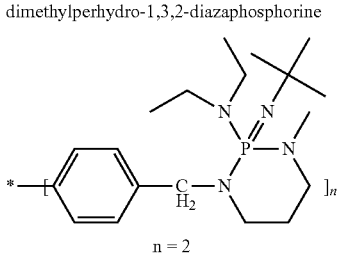

n = 2
2-tert-butylimino-2-diethylamino-1,3-dimethylperhydro-1,3,2-diazaphosphorine

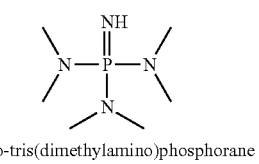

imino-tris(dimethylamino)phosphorane

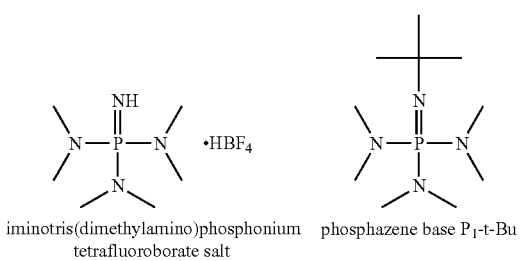

iminotris(dimethylamino)phosphonium tetrafluoroborate salt    phosphazene base P$_1$-t-Bu

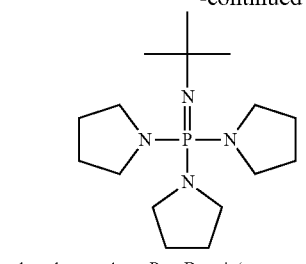

phosphazene base P$_1$-t-Bu-tris(tertramethylene) purum

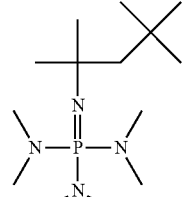

phosphazene base P$_1$-t-Oct

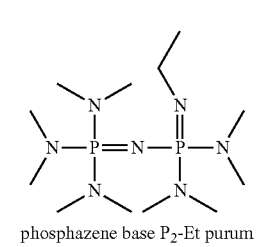

phosphazene base P$_2$-Et purum

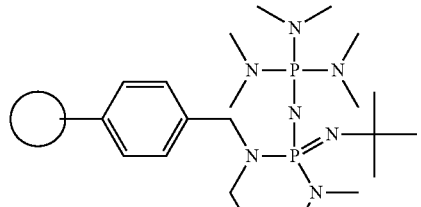

phosphazene base P$_2$-t-Bu

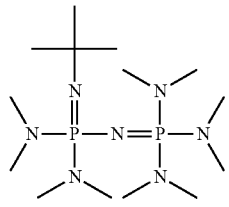

phosphazene base P$_2$-t-Bu

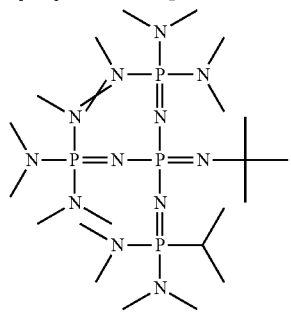

phosphazene base P$_4$-t-Bu

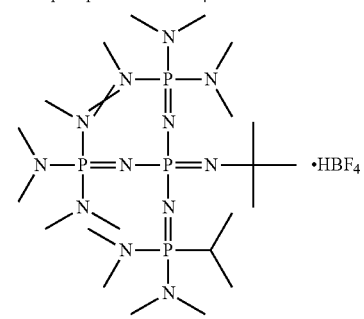

phosphazene base P$_4$-t-Bu tetrafluoroborate salt

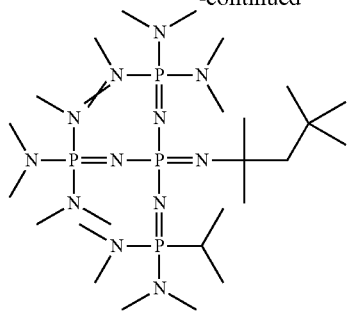

phosphazene base P$_4$-t-Oct

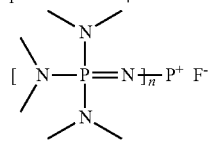

n = 4 tetrakis[tris(dimethylamino)phosphoranylidenamino] phosphonium fluoride

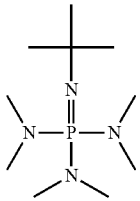

tert-butylimino-tris(dimethylamino)phosphorane and the like, and combinations thereof. Preferred photoactivatable compositions include those that can generate phosphazenes such as 2-tert-butylimino-2-diethylamino-1,3-dimethylperhydro-1,3,2-diazaphosphorine, phosphazene base P$_1$-t-Bu-tris(tetramethylene), phosphazene base P$_4$-t-Bu, and combinations thereof.

Useful photoactivatable compositions also further include those that, upon exposure to radiation, generate proazaphosphatrane bases (Verkade's bases) that can be represented by the following general formula:

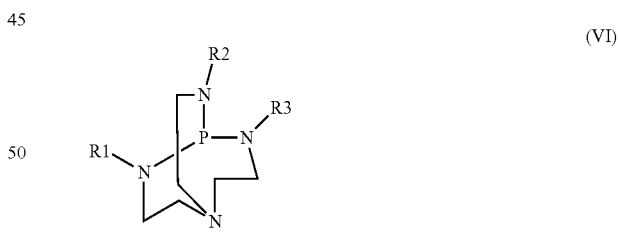

(VI)

wherein R1, R2, and R3 are each independently selected from hydrogen, monovalent organic groups, monovalent heteroorganic groups (for example, comprising nitrogen, oxygen, phosphorus, or sulfur in the form of groups or moieties that are bonded through a carbon atom and that do not contain acid functionality such as carboxylic or sulfonic), and combinations thereof (less preferably hydrogen). The organic and heteroorganic groups preferably have from 1 to about 20 carbon atoms (more preferably, from 1 to about 10 carbon atoms; most preferably, from 1 to about 6 carbon atoms).

Representative examples of useful photoactivatable compositions include those that can generate proazaphosphatrane compounds such as

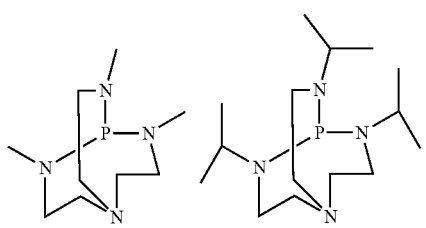

2,8,9-trimethyl-2,5,8,9-tretraaza-1-phosphabicyclo[3.3.3]undecane 2,8,9-triisopropyl-2,5,8,9-tetraaza-1-phosphabicyclo [3.3.3.]undecane

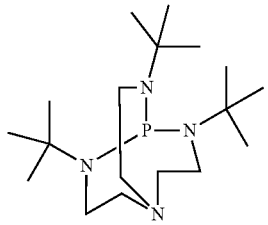

2,8,9-triisobutyl-2,5,8,9-tetraaza-1-phosphabicyclo [3.3.3.]undecane and the like, and combinations thereof. Preferred photoactivatable compositions include those that can generate 2,8,9-triisopropyl-2,5,8,9-tetraaza-1-phosphabicyclo[3.3.3]undecane.

Suitable photoactivatable compositions for use in generating the above-described bases are known. For example, salts that can generate amidine or guanidine bases upon thermal activation (for example, at elevated temperatures or upon exposure to infrared radiation) are described in U.S. Pat. No. 5,219,958 (Noomen et al.), the descriptions of which salts are incorporated herein by reference. A quaternary ammonium salt (namely, 8-(4'-benzoylphenylmethyl)-8-azania-1-aza-bicyclo[5.4.0]undec-7-ene benzo[o]mate) that generates DBU upon irradiation has been described by K. Suyama et al., Journal of Photopolymer Science and Technology 19(1), 81 (2006), the description of this salt and its synthesis being incorporated herein by reference. U.S. Pat. No. 6,124,371 (Stanssens et al.) describes photolabile compounds of the structural formula Z-A (wherein Z is a photolabile group, A is a strong base, and Z is covalently bound to A) that can liberate amidine or guanidine bases upon irradiation (for example, ultraviolet light, electron beam, infrared, or laser irradiation), the descriptions of which compounds are also incorporated herein by reference.

U.S. Pat. No. 6,277,986 (Hall-Goule et al.) describes α-amino ketones (comprising an aromatic or heteroaromatic radical that is capable of absorbing light in the wavelength range of 200 to 650 nanometers (nm)) from which amidine bases can be liberated upon irradiation (with visible or ultraviolet light), the descriptions of which ketones are incorporated herein by reference. U.S. Pat. No. 6,551,761 (Hall-Goule et al.) describes photoactivatable nitrogen-containing salts including tetraaryl- and triarylalkylborate salts of, for example, α-amidinium ketones. The photoactivatable salts can release amidine, guanidine, or phosphazene (and apparently, by extension, proazaphosphatrane) bases upon exposure to visible or ultraviolet light, the descriptions of the photoactivatable salts being incorporated herein by reference.

Preferred photoactivatable compositions for use in the curable composition of the invention include those described in U.S. Pat. No. 7,538,104 (Baudin et al.), the descriptions of which compositions (and methods for their preparation) are incorporated herein by reference. The compositions comprise at least one 1,3-diamine compound that is substituted on at least one nitrogen atom by at least one aralkyl radical. The aralkyl radical preferably comprises at least one aromatic or heteroaromatic radical that absorbs light in the wavelength range of 200 nm to 650 nm. Absorption of the light results in a photoelimination that leads to the generation of an amidine or guanidine.

A preferred class of such photoactivatable compositions comprises at least one 1,3-diamine compound selected from those that are represented by the formula $$N(R_7)(R_6)-CH(R_5)-N(R_4)-C(R_1)(R_2)(R_3) \quad (VII)$$

wherein $R_1$ is selected from aromatic radicals, heteroaromatic radicals, and combinations thereof that absorb light in the wavelength range from 200 nm to 650 nm and that are unsubstituted or substituted one or more times by at least one monovalent group selected from $C_1$-$C_{18}$ alkyl, $C_2$-$C_{18}$ alkenyl, $C_2$-$C_{18}$ alkynyl, $C_1$-$C_{18}$ haloalkyl, —$NO_2$, —$NR_{10}R_{11}$, —CN, —$OR_{12}$, —$SR_{12}$, —$C(O)R_{13}$, —$C(O)OR_{14}$, halogen, groups of the formula $N(R_7)(R_6)$—$CH(R_5)$—$N(R_4)$—$C(R_2)(R_3)$— where $R_2$-$R_7$ are as defined for Formula VII, and combinations thereof, and that upon said absorption bring about a photoelimination that generates an amidine or guanidine; $R_2$ and $R_3$ are each independently selected from hydrogen, $C_1$-$C_{18}$ alkyl, phenyl, substituted phenyl (that is, substituted one or more times by at least one monovalent group selected from $C_1$-$C_{18}$ alkyl, —CN, —$OR_{12}$, —$SR_{12}$, halogen, $C_1$-$C_{18}$ haloalkyl, and combinations thereof), and combinations thereof; $R_5$ is selected from $C_1$-$C_{18}$ alkyl, —$NR_8R_9$, and combinations thereof; $R_4$, $R_6$, $R_7$, $R_8$, $R_9$, $R_{10}$ and $R_{11}$ are each independently selected from hydrogen, $C_1$-$C_{18}$ alkyl, and combinations thereof; or $R_4$ and $R_6$ together form a $C_2$-$C_{12}$ alkylene bridge that is unsubstituted or is substituted by one or more monovalent groups selected from $C_1$-$C_4$ alkyl radicals and combinations thereof; or $R_5$ and $R_7$, independently of $R_4$ and $R_6$, together form a $C_2$-$C_{12}$ alkylene bridge that is unsubstituted or is substituted by one or more monovalent groups selected from $C_1$-$C_4$ alkyl radicals and combinations thereof; or, if $R_5$ is —$NR_8R_9$, then $R_7$ and $R_9$ together form a $C_2$-$C_{12}$ alkylene bridge that is unsubstituted or is substituted by one or more monovalent groups selected from $C_1$-$C_4$ alkyl radicals and combinations thereof; $R_{12}$ and $R_{13}$ are each independently selected from hydrogen, $C_1$-$C_{19}$ alkyl, and combinations thereof; and $R_{14}$ is selected from $C_1$-$C_{19}$ alkyl and combinations thereof.

The alkyl and haloalkyl groups can be linear or branched and, preferably, contain 1 to about 12 carbon atoms (more preferably, 1 to about 6 carbon atoms). Halogen atoms preferably are chlorine, fluorine, and/or bromine (more preferably, chlorine and/or fluorine). The alkenyl groups can be linear or branched and, preferably, contain 2 to about 12 carbon atoms (more preferably, 2 to about 6 carbon atoms). The alkynyl groups can be linear or branched and, preferably, contain 2 to about 12 carbon atoms (more preferably, 2 to about 6 carbon atoms).

Preferred 1,3-diamine compounds of Formula VII include those wherein $R_1$ is selected from substituted and unsubstituted phenyl, naphthyl, phenanthryl, anthryl, pyrenyl, 5,6,7,8-tetrahydro-2-naphthyl, 5,6,7,8-tetrahydro-1-naphthyl, thienyl, benzo[b]thienyl, naphtho[2,3-b]thienyl, thianthrenyl, anthraquinonyl, dibenzofuryl, chromenyl, xanthenyl, thioxanthyl, phenoxathiinyl, pyrrolyl, imidazolyl, pyrazolyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, terphenyl, stilbenzyl, fluorenyl, phenoxazinyl, and combinations thereof, these radicals being unsubstituted or substituted one or more times by $C_1$-$C_{18}$ alkyl, $C_2$-$C_{18}$ alkenyl, $C_2$-$C_{18}$ alkynyl, $C_1$-$C_{18}$ haloalkyl, —$NO_2$, —$NR_{10}R_{11}$, —CN, —$OR_{12}$, —$SR_{12}$, —$C(O)R_{13}$, —$C(O)OR_{14}$, halogen, a radical of the formula $N(R_7)(R_6)$—$CH(R_5)$—$N(R_4)$—$C(R_2)(R_3)$—, or a combination thereof, where $R_2$-$R_7$ and $R_{10}$-$R_{14}$ are as defined for Formula VII, or $R_1$ is a substituted or unsubstituted biphenylyl radical, wherein each phenyl group is independently substituted with from zero to three (preferably, zero or one) substituents selected from $C_1$-$C_{18}$ alkyl, $C_2$-$C_{18}$ alkenyl, —OH, —CN, —$OR_{10}$, —$SR_{10}$, halogen, radicals of the formula $N(R_7)(R_6)$—$CH(R_5)$—$N(R_4)$—$C(R_2)(R_3)$—, and combinations thereof, where $R_2$-$R_7$ and $R_{10}$-$R_{14}$ are as defined for Formula VII.

More preferably, $R_1$ is selected from substituted and unsubstituted phenyl, naphthyl, anthryl, anthraquinon-2-yl, biphenylyl, pyrenyl, thioxanthyl, thianthrenyl, phenothiazinyl, and combinations thereof (even more preferably, $R_1$ is selected from substituted and unsubstituted phenyl, anthryl, naphthyl, anthraquinon-2-yl, biphenylyl, and combinations thereof; still more preferably, $R_1$ is selected from phenyl, 4-methylphenyl, biphenylyl, 2,4,6-trimethylphenyl, 4-cyanophenyl, 3-cyanophenyl, 2-chlorophenyl, 2,6-dichlorophenyl, 3-methoxyphenyl, 4-methoxyphenyl, 4-ethenylphenyl, 4-methylthiophenyl, 4-trifluoromethylphenyl, 2-nitrophenyl, 2,4,6-trimethoxyphenyl, 2,4-dimethoxyphenyl, naphthyl, anthryl, anthraquinon-2-yl, and combinations thereof, or is selected from the aforementioned radicals substituted with a radical of the formula $N(R_7)(R_6)$—$CH(R_5)$—$N(R_4)$—$C(R_2)(R_3)$—, where $R_2$-$R_7$ are as defined for Formula VII; most preferably, $R_1$ is selected from phenyl, 3-methoxyphenyl, 4-methoxyphenyl, 2,4,6-trimethoxyphenyl, 2,4-dimethoxyphenyl, and combinations thereof).

Preferably, $R_2$ and $R_3$ each are independently selected from hydrogen, $C_1$-$C_6$ alkyl, and combinations thereof (more preferably, both are hydrogen); $R_4$ and $R_6$ together form a $C_2$-$C_6$ alkylene (preferably, $C_3$ alkylene) bridge that is unsubstituted or is substituted by one or more groups selected from $C_1$-$C_4$ alkyl radicals and combinations thereof; and/or $R_5$ and $R_7$ together form a $C_2$-$C_6$ alkylene (preferably, $C_3$ or $C_5$ alkylene) bridge that is unsubstituted or is substituted by one or more groups selected from $C_1$-$C_4$ alkyl radicals and combinations thereof, or, if $R_5$ is —$NR_8$, $R_9$ (which is less preferable, as guanidine bases are somewhat less preferred than amidine bases), $R_9$ and $R_7$ together form a $C_2$-$C_6$ alkylene bridge that is unsubstituted or substituted by one or more groups selected from $C_1$-$C_4$ alkyl radicals and combinations thereof.

Representative examples of useful photoactivatable compositions include those that comprise at least one compound selected from 5-benzyl-1,5-diazabicyclo[4.3.0]nonane, 5-(anthracen-9-yl-methyl)-1,5-diaza[4.3.0]nonane, 5-(2'-nitrobenzyl)-1,5-diazabicyclo[4.3.0]nonane, 5-(4'-cyanobenzyl)-1,5-diazabicyclo[4.3.0]nonane, 5-(3'-cyanobenzyl)-1,5-diazabicyclo[4.3.0]nonane, 5-(anthraquinon-2-yl-methyl)-1,5-diaza[4.3.0]nonane, 5-(2'-chlorobenzyl)-1,5-diazabicyclo[4.3.0]nonane, 5-(4'-methylbenzyl)-1,5-diazabicyclo[4.3.0]nonane, 5-(2',4',6'-trimethylbenzyl)-1,5-diazabicyclo[4.3.0]nonane, 5-(4'-ethenylbenzyl)-1,5-diazabicyclo[4.3.0]nonane, 5-(3'-trimethylbenzyl)-1,5-diazabicyclo[4.3.0]nonane, 5-(2',3'-dichlorobenzyl)-1,5-diazabicyclo[4.3.0]nonane, 5-(naphth-2-yl-methyl-1,5-diazabicyclo[4.3.0]nonane, 1,4-bis(1,5-diazabicyclo[4.3.0]nonanylmethyl)benzene, 8-benzyl-1,8-diazabicyclo[5.4.0]undecane, 8-benzyl-6-methyl-1,8-diazabicyclo[5.4.0]undecane, 9-benzyl-1,9-diazabicyclo[6.4.0]dodecane, 10-benzyl-8-methyl-1,10-diazabicyclo[7.4.0]tridecane, 11-benzyl-1,1'-diazabicyclo[8.4.0]tetradecane, 8-(2'-chlorobenzyl)-1,8-diazabicyclo[5.4.0]undecane, 8-(2',6'-dichlorobenzyl)-1,8-diazabicyclo[5.4.0]undecane, 4-(diazabicyclo[4.3.0]nonanylmethyl)-1,1'-biphenyl, 4,4'-bis(diazabicyclo[4.3.0]nonanylmethyl)-11'-biphenyl, 5-benzyl-2-methyl-1,5-diazabicyclo[4.3.0]nonane, 5-benzyl-7-methyl-1,5,7-triazabicyclo[4.4.0]decane, and the like, and combinations thereof.

A preferred group of photoactivatable compositions includes those that comprise at least one compound selected from 5-benzyl-1,5-diazabicyclo[4.3.0]nonane, 5-(anthracen-9-yl-methyl)-1,5-diaza[4.3.0]nonane, 5-(2'-nitrobenzyl)-1,5-diazabicyclo[4.3.0]nonane, 5-(4'-cyanobenzyl)-1,5-diazabicyclo[4.3.0]nonane, 5-(3'-cyanobenzyl)-1,5-diazabicyclo[4.3.0]nonane, 5-(anthraquinon-2-yl-methyl)-1,5-diaza[4.3.0]nonane, 5-(2'-chlorobenzyl)-1,5-diazabicyclo[4.3.0]nonane, 5-(4'-methylbenzyl)-1,5-diazabicyclo[4.3.0]nonane, 5-(2',4',6'-trimethylbenzyl)-1,5-diazabicyclo[4.3.0]nonane, 5-(4'-ethenylbenzyl)-1,5-diazabicyclo[4.3.0]nonane, 5-(3'-trimethylbenzyl)-1,5-diazabicyclo[4.3.0]nonane, 5-(2',3'-dichlorobenzyl)-1,5-diazabicyclo[4.3.0]nonane, 5-(naphth-2-yl-methyl-1,5-diazabicyclo[4.3.0]nonane, 1,4-bis(1,5-diazabicyclo[4.3.0]nonanylmethyl)benzene, 8-benzyl-1,8-diazabicyclo[5.4.0]undecane, 8-benzyl-6-methyl-1,8-diazabicyclo[5.4.0]undecane, 8-(2'-chlorobenzyl)-1,8-diazabicyclo[5.4.0]undecane, 8-(2',6'-dichlorobenzyl)-1,8-diazabicyclo[5.4.0]undecane, 4-(diazabicyclo[4.3.0]nonanylmethyl)-1,1'-biphenyl, 4,4'-bis(diazabicyclo[4.3.0]nonanylmethyl)-11'-biphenyl, 5-benzyl-2-methyl-1,5-diazabicyclo[4.3.0]nonane, 5-benzyl-7-methyl-1,5,7-triazabicyclo[4.4.0]decane, and combinations thereof.

A second preferred group of photoactivable compositions includes those that comprise at least one compound selected from 8-benzyl-1,8-diazabicyclo[5.4.0]undecane, 8-benzyl-6-methyl-1,8-diazabicyclo[5.4.0]undecane, 9-benzyl-1,9-diazabicyclo[6.4.0]dodecane, 10-benzyl-8-methyl-1,10-diazabicyclo[7.4.0]tridecane, 11-benzyl-1,1'-diazabicyclo[8.4.0]tetradecane, and combinations thereof. Most preferred are photoactivatable compositions that comprise at least one compound selected from 8-benzyl-1,8-diazabicyclo[5.4.0]undecane, 8-benzyl-6-methyl-1,8-diazabicyclo[5.4.0]undecane, and combinations thereof.

The photoactivatable compositions can optionally (but preferably) further comprise at least one photosensitizer (for example, a compound having an absorption spectrum that overlaps or closely matches the emission spectrum of the radiation source to be used and that can improve the overall quantum yield by means of, for example, energy transfer or electron transfer to other component(s) of the photoactivatable composition). Useful photosensitizers include aromatic ketones (for example, substituted or unsubstituted benzophenones, substituted or unsubstituted thioxanthones, substituted or unsubstituted anthraquinones, and the like, and combinations thereof), dyes (for example, oxazines, acridines, phenazines, rhodamines, and the like, and combinations thereof), and the like, and combinations thereof. Preferred photosensitizers include aromatic ketones and combinations thereof (more preferably, substituted or unsubstituted benzophenones, substituted or unsubstituted thioxanthones, and combinations thereof; most preferably, substituted or unsubstituted benzophenones and combinations thereof). The amount of photosensitizer can vary widely, depending upon, for example, its nature, the nature of other component(s) of the photoactivatable composition, and the particular curing conditions. For example, amounts ranging from about 0.1 weight percent to about 0.5 weight percent can be useful for some applications.

Preparation of Curable Composition

The curable composition of the invention can be prepared by combining components (a), (b), and (c) in essentially any order (preferably, with agitation or stirring). Preferably, components (a) and (b) are combined initially, followed by addition of component (c). The composition can be maintained as a relatively shelf-stable, 1-part system (comprising all three components) in the substantial absence of radiation of an activating wavelength. The composition can be stable under such conditions for periods of up to, for example, days or weeks (a relatively long pot life), prior to coating or other application of the composition, with or without the addition of solvent (which is optional).

The relative amounts of components (a) and (b) can vary widely, depending upon their nature and the desired properties of the curable and/or cured composition. Although stoichiometry prescribes a 1:1 molar ratio of reactive silane functionality (for example, one mole of hydrosilyl moieties for every mole of hydroxysilyl moieties), in practice it can be useful to have a deficiency or an excess of hydrosilyl functionality (for example, this can be useful when cure inhibitors are present). Molar ratios (of hydrosilyl moieties to hydroxysilyl moieties) up to, for example, about 8:1 or about 13:1 or even as high as about 35:1 can be useful. Component (c) (the photoactivatable composition(s)) can be present in the curable composition in amounts ranging, for example, from about 0.1 to about 10 weight percent (preferably, from about 0.1 to about 5 weight percent; more preferably, from about 0.5 to about 2 weight percent), based upon the total weight of components (a), (b), and (c).

If desired, the curable composition can comprise at least one solvent or diluent to aid in storage stability, mixing, and/or coating, particularly when components (a) and (b) are polymeric. Suitable solvents for use in the curable composition of the invention include aprotic solvents such as aromatic solvents (for example, xylene, toluene, 1,2-dichlorobenzene, 1,3-dichlorobenzene, 1,4-dichlorobenzene, and the like, and mixtures thereof), ketones (for example, methyl ethyl ketone (MEK), cyclohexanone, and the like, and mixtures thereof), alkyl esters (for example, ethyl acetate, butyl acetate, and the like, and mixtures thereof), alkanes (for example, heptane, isoparaffinic hydrocarbons, and the like, and mixtures thereof), ethers (for example, t-butyl methyl ether, tetrahydrofuran (THF), and the like, and mixtures thereof), and the like, and mixtures thereof. Preferred solvents include aromatic solvents, alkanes, ketones, and mixtures thereof with xylene, heptane, methyl ethyl ketone, and mixtures thereof being more preferred and heptane, methyl ethyl ketone, and mixtures thereof most preferred.

Minor amounts of optional components can be added to the curable composition to impart particular desired properties for particular curing methods or uses. Useful compositions can comprise conventional additives such as, for example, catalysts (including conventional condensation catalysts such as tin catalysts, which can be added as co-catalysts if desired), initiators, surfactants, stabilizers, thermal inhibitors, antioxidants, flame retardants, adhesion promoters, release modifiers (for example, silicate MQ resin), colorants, and the like, and mixtures thereof.

Use and Curing of Curable Composition

The curable composition of the invention can be used in various different applications. For example, the composition(s) can be used as sealants, release coatings, surface treatments, hardcoats, and the like. When used as fluorinated surface treatments, a degree of hydrophobicity and/or oleophobicity can be imparted to a variety of substrates (for example, for surface protection or to enhance ease of cleaning).

The curable composition of the invention (or, alternatively, its components) can be applied to at least a portion of at least one major surface of a substrate (for example, a sheet, a fiber, or a shaped object) by essentially any known or hereafter-developed application method, so as to form a variety of different coated articles. The composition can be applied in essentially any manner (and with essentially any thickness) that can form a useful coating.

Useful application methods include coating methods such as dip coating, spin coating, spray coating, wiping, roll coating, and the like, and combinations thereof. The composition can be applied in neat form or in the form of solvent solutions (for example, in solvents such as alkyl esters, ketones, alkanes, aromatics, and the like, and mixtures thereof). When solvent is used, useful concentrations of the composition can vary over a wide range (for example, from about 1 to about 90 weight percent), depending upon the viscosity of the composition, the application method utilized, the nature of the substrate, and the desired properties.

Substrates suitable for use in preparing the coated articles include those having at least one surface comprising a material that is solid and preferably substantially inert to any coating or application solvent that is used. Preferably, the curable composition can adhere to the substrate surface through chemical interactions, physical interactions, or a combination thereof (more preferably, a combination thereof).

Suitable substrates can comprise a single material or a combination of different materials and can be homogeneous or heterogeneous in nature. Useful heterogeneous substrates include coated substrates comprising a coating of a material (for example, a metal or a primer) borne on a physical support (for example, a polymeric film).

Useful substrates include those that comprise wood, glass, minerals (for example, both man-made ceramics such as concrete and naturally-occurring stones such as marble and the like), polymers (for example, polycarbonate, polyester, polyacrylate, and the like), metals (for example, copper, silver, gold, aluminum, iron, stainless steel, nickel, zinc, and the like), metal alloys, metal compounds (for example, metal oxides and the like), leather, parchment, paper, textiles, painted surfaces, and combinations thereof. Preferred substrates include glass, minerals, wood, metals, metal alloys, metal compounds, polymers, and combinations thereof (more preferably, metals, metal alloys, metal compounds, polymers, and combinations thereof).

Preferred substrates include those used for pressure-sensitive adhesive (PSA) products. For example, the curable composition can be applied to suitable flexible or inflexible backing materials and then cured. Useful flexible backing materials include paper, Kraft paper, polyolefin-coated paper, plastic films (for example, poly(propylene), poly(ethylene), poly(vinyl chloride), polyester (including poly(ethylene terephthalate), polyamide, cellulose acetate, and ethyl cellulose), and the like, and combinations thereof, although essentially any surface requiring release toward adhesives can be utilized. Backings can thus also be of woven fabric formed of threads of synthetic or natural materials such as cotton, nylon, rayon, glass, or ceramic material, or they can be of nonwoven fabric such as air-laid webs of natural or synthetic fibers or blends of these. In addition, suitable backings can be formed of metal, metallized polymeric film, or ceramic sheet material. Primers can be utilized, but they are not always necessary.

The curable composition of the invention can provide coatings that are suitable for use in the manufacture of PSA-coated labels and tapes. The specific level of release provided upon curing can be controllably varied through variation in, for example, the weight percentage and molecular weight of component (a) of the composition, or through the addition of release modifiers (for example, silicate MQ resin), which also can be varied in nature and/or amount.

The curable composition can be cured by exposing at least a portion of the composition to radiation of an appropriate wavelength to activate the photoactivatable composition. The preferred curing conditions will vary, depending upon the particular application and its accompanying requirements and conditions. Moisture can be present but generally is not necessary.

The preferred radiation source and exposure time will vary depending upon, for example, the nature and amount of the photoactivatable composition. Sources of ultraviolet, visible, and/or infrared radiation can be useful (for example, wavelengths ranging from about 200 nm to about 650 or 700 nm or up to about 20,000 nm; preferably, ultraviolet radiation, visible radiation, or a combination thereof). Suitable radiation includes sunlight and light from artificial sources, including both point sources and flat radiators.

Representative examples of useful radiation sources include carbon arc lamps; xenon arc lamps; medium-pressure, high-pressure, and low-pressure mercury lamps, doped if desired with metal halides (metal halogen lamps); microwave-stimulated metal vapor lamps; excimer lamps; superactinic fluorescent tubes; fluorescent lamps; incandescent argon lamps; electronic flashlights; xenon flashlights; photographic flood lamps; electron beams; X-rays, produced by means of synchrotrons or laser plasma; laser light sources (for example, excimer lasers); and the like; and combinations thereof. The distance between the radiation source and the coated substrate can vary widely, depending upon the particular application and the type and/or power of the radiation source (for example, distances ranging from about 2 cm to about 150 cm can be useful).

Cure generally can be effected by carrying out irradiation and/or subsequent processing of the coated substrate at temperatures ranging from room temperature (for example, about 20-23° C.) up to about 150° C. or more (preferably, temperatures of about 20° C. to about 125° C.; more preferably, about 20° C. to about 100° C.; most preferably, about 20° C. to about 80° C.). Curing times can range from a few seconds or less (for example, at room temperature with adequate amounts of catalyst and light exposure) to minutes or hours (for example, under low catalyst and/or low light conditions).

Release coatings obtained via cure of the curable composition of the invention generally contain little or no free silicone to adversely affect the tack and peel properties of PSAs that come in contact with them. The curable composition of the invention can cure relatively rapidly to provide relatively firmly anchored, highly crosslinked, solvent-resistant, tack-free coatings, which can be used with a broad range of PSA types (for example, acrylates, tackified natural rubbers, and tackified synthetic elastomers).

Articles in the form of PSA laminates (for example, comprising a layer of PSA borne on a release liner) can be prepared by placing a PSA layer in contact with the release coating through dry lamination, wet solution casting, or even by application of a photopolymerizable composition to the release coating, followed by irradiation to effect photopolymerization (for example, as described in U.S. Pat. No. 4,181,752 (Martens et al.), the description of which is incorporated herein by reference). Such articles can exhibit relatively good storage stability (as evidenced, for example, by the results of room temperature and/or heat accelerated aging tests to evaluate any change in the level of release (peel force) from the release coating and/or in the subsequent level of adhesion to a desired substrate).

EXAMPLES

Objects and advantages of this invention are further illustrated by the following examples, but the particular materials and amounts thereof recited in these examples, as well as other conditions and details, should not be construed to unduly limit this invention. These examples are merely for illustrative purposes only and are not meant to be limiting on the scope of the appended claims.

Materials

Unless otherwise noted, all parts, percentages, ratios, etc., in the examples and in the remainder of the specification are by weight. Unless otherwise noted, all chemicals were obtained from, or are available from, chemical suppliers such as Aldrich Chemical Company, Milwaukee, Wis.

Preliminary Screening of Bases 1-10 and Comparative Bases C-1-C-12

A sample of a 30 weight percent solids dispersion of a blend of reactive hydroxysilyl-functional siloxane polymer(s) (said to comprise hydroxyl-terminated polydimethylsiloxane) and hydrosilyl-functional polysiloxane crosslinker (said to comprise poly(methyl)(hydrogen)siloxane) in xylene (a premium release coating composition obtained from Dow Corning Corporation, Midland, Mich., under the trade designation Syl-Off™ 292) was diluted to 10 weight percent solids with heptane. For each of Bases 1-10 and Comparative Bases C-1-C-12, 0.02 g of base (listed in Table 1 below; all bases were obtained from Aldrich Chemical Company, Milwaukee, Wis.) was added to 5 g of Syl-Off™ 292 solution (10 weight percent in heptane) and then mixed. The resulting mixtures were coated on the primed side of a 50 micrometer thick polyester terephthalate (PET) film (obtained from Mitsubishi Polyester Film, Greer, SC, under the trade designation Hostaphan™ 3SAB, referred to hereinafter as 3SAB PET film, which has one side chemically treated or primed to improve the adhesion of silicone coatings) using a number 4 rod. The resulting coated 3SAB PET samples were set aside at room temperature (about 23° C.) and their curing status (level of tackiness) was monitored. A coated sample was deemed cured if the coating solidified within 5 minutes. A coated sample was deemed not cured if the coating did not solidify and remained tacky for at least 24 hours at room temperature. The results of the base screening are shown in Table 1 below.

TABLE 1

| Base No. | Base | Curing |
|---|---|---|
| 1 | DBU (1,8-Diazabicyclo[5.4.0]undec-7-ene) | Yes |

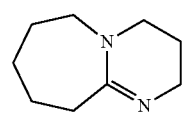 [SMILES: C1CCC2=NCCCN2CC1]

TABLE 1-continued

| Base No. | Base | Curing |
|---|---|---|
| 2 | DBN (1,5-Diazabicyclo[4.3.0]non-5-ene) | Yes |
| 3 | 1,2-Dimethyl-1,4,5,6-tetrahydropyrimidine | Yes |
| 4 | TBD (1,5,7-Triazabicyclo[4.4.0]dec-5-ene) | Yes |
| 5 | MTBD (7-Methyl-1,5,7-triazabicyclo[4.4.0]dec-5-ene) | Yes |
| 6 | 2-tert-Butyl-1,1,3,3-tetramethylguanidine | Yes |
| 7 | Phosphazene base P$_1$-t-Bu-tris(tetramethylene) | Yes |
| 8 | Phosphazene base P$_4$-t-Bu solution (1M in Hexane) | Yes |
| 9 | 2-tert-Butylimino-2-diethylamino-1,3-dimethylperhydro-1,3,2-diazaphosphorine | Yes |
| 10 | 2,8,9-Triisopropyl-2,5,8,9-tetraaza-1-phosphabicyclo[3,3,3]undecane | Yes |
| C-1 | 1,1,3,3-Tetramethylguanidine | No |
| C-2 | N,N'-Diisopropylcarbodiimide | No |
| C-3 | N,N'-Dicyclohexylcarbodiimide | No |
| C-4 | Imidazole | No |
| C-5 | N-Methylimidazole | No |
| C-6 | 1,2-Dimethylimidazole | No |

TABLE 1-continued

| Base No. | Base | Curing |
|---|---|---|
| C-7 | 1,4-Diazabicyclo[2.2.2]octane 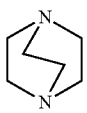 | No |
| C-8 | 4,4'-Trimethylenebis(1-methylpiperidine) 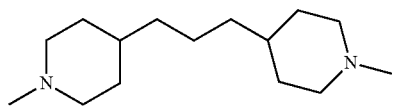 | No |
| C-9 | 2,6-Dimethylpyridine 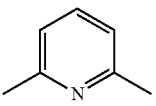 | No |
| C-10 | 4-Dimethylaminopyridine 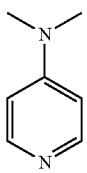 | No |
| C-11 | 2,2,6,6-Tetramethylpiperidine 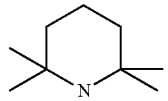 | No |
| C-12 | 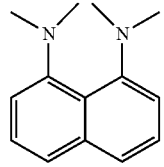 [SMILES: CN(C)c1cccc2cccc(N(C)C)c12] | No |

Test Method for Measuring Aced Release and Subsequent Adhesion

These tests measured the effectiveness of release liners that had been aged for a period of time at a constant temperature and relative humidity. The aged release value is a quantitative measure of the force required to remove a flexible adhesive tape from the release liner at a specific angle and rate of removal. This force is expressed in Newtons per decimeter (N/dm). Unless otherwise noted, one of the following four adhesive tapes was used to measure the aged release value and the subsequent adhesion (sometimes called readhesion) to a substrate.

Tape I is an acrylic pressure-sensitive adhesive tape comprising a polypropylene backing commercially available from 3M Company, St. Paul, Minn. under the trade designation Scotch™ Magic™ Tape 810.

Tape II is an acrylic pressure-sensitive adhesive tape comprising a polypropylene backing commercially available from 3M Company, St. Paul, Minn. under the trade designation Scotch™ Book Tape 845.

Release liners (release-coated substrates) of the invention were tested for their aged release values by lamination of one of the above-described adhesive tapes, with the release coating of the release liner facing the adhesive-bearing side of the tape. The resulting laminates were cut into test strips about 2.54 cm wide and approximately 12 cm long. The test strips were then aged for a period of time at a constant temperature and relative humidity (RH), as specified in the various examples below. The aged test strips were attached to the working platen of a slip/peel tester (Model SP2000, obtained from Instrumentors, Inc., Strongsville, Ohio) using a 2.54 cm wide double-coated adhesive paper tape (commercially available from 3M Company, St. Paul, Minn. under the trade designation 3M™ Double Coated Paper Tape 410B) applied to the release liner side of the test strip. The attached test strip was rolled once on the working platen with a 2 kg rubber roller. The adhesive tape of the test strip was then removed from the release liner by peeling at 180 degrees and a rate of 2.3 meters per minute (90 inches per minute), and the force required for removing the adhesive tape from the release liner was measured over a five-second data collection time.

All release tests were carried out in a facility at constant temperature (23° C.) and constant relative humidity (50 percent). At least two measurements were made for each example, and the data are reported as an average of all measurements. Measurements were made in grams-force/inch and converted to N/dm.

After peeling of the adhesive tape from the release liner, the subsequent (180 degree peel) adhesion of the adhesive tape was measured by adhering the freshly peeled adhesive tape (without the release liner) to a float glass test panel, with the adhesive-bearing side of the tape in contact with the panel. The adhered adhesive tape was rubbed down on the test panel, first using light thumb pressure and then with a 2 kg rubber roller at a rate of 61 cm per minute. The subsequent adhesion value of the tape was then measured using the above-described instrument and test parameters. These measurements were taken to determine whether a drop in adhesion value occurred due to undesirable contamination of the adhesive surface by the release coating of the release liner. The subsequent adhesion test was also carried out at 23° C. and 50 percent relative humidity. At least two measurements were made for each example, and the data are reported as an average of all measurements. Measurements were made in grams-force/inch and converted to N/dm.

Example 1

A mixture of 34.0 g (0.2 mol) 1,8-diazabicylo[5.4.0]undecene and 200 mL toluene was mixed with 34.2 g (0.2 mol) benzyl bromide. An insoluble oil formed and then changed to a white solid as the temperature rose to 57° C. over 10 minutes. After 4 hours, the solid was filtered and dried to provide 62.5 g of 8-benzyl-1,8-diazabicyclo[5.4.0]undecane (the 8-benzyl salt of DBU, which was soluble in water). NaBH$_4$ solution (1.58 g, 5.1 mmol, 4.4M NaBH$_4$ in 14M NaOH solution, obtained from Alfa Aesar, Ward Hill, Mass.) was diluted with 10 mL water. Then, 15 mL t-butyl methyl ether (t-BuOMe) was added to the diluted solution, and the resulting mixture was magnetically stirred and cooled to 3° C. To the cooled mixture was added 3.23 g of the 8-benzyl salt of DBU prepared as described above. After 2 hours, the resulting cold mixture was phase split, the resulting aqueous layer was extracted with t-BuOMe, and the resulting t-BuOMe solutions were combined, dried, and stripped to yield 0.86 g of a product (photolatent catalyst mixture). Gas-liquid chromatographic (GLC) analysis of the product indicated that it contained 39 percent 8-benzyl-1,8-diazabicyclo[5.4.0]undecane (GLC area response with a thermal conductivity detector;

identified by gas chromatography/mass spectrometry (GC/MS) analysis), 13 percent of N-3-benzylaminopropylazepine (identified by GC/MS and nuclear magnetic resonance (NMR) analysis), and 48 percent of what was believed to be N-(3-benzylaminopropyl)azepin-2-one (GC/MS mass of 262).

9 g of Syl-Off™ 292 release coating composition, 0.45 g of the photolatent catalyst mixture prepared as described above (containing 39 percent 8-benzyl-1,8-diazabicyclo[5.4.0]undecane), 16.34 g heptane, 4.1 g methyl ethyl ketone (MEK), and 0.11 g benzophenone were weighed into a 120 mL glass jar. The glass jar was shaken until the contents were homogeneous. The resulting homogeneous mixture was coated on the primed side of a 50 micrometers thick 3SAB PET film.

The coated film was taped to a backer board and then passed twice through an ultraviolet (UV) process chamber (Model MC-6RQN, available from Fusion UV Systems, Inc., Gaithersburg, Md.) equipped with a 200 Watts per centimeter, mercury lamp (H-bulb) at a rate of 12 meters per minute. The lamp was positioned about 15 cm above the coated film. The UV process chamber was blanketed with nitrogen to lower the oxygen levels. Before entering the UV process chamber, the coating on the film was not cured and could be smeared off when rubbed by fingers. After the first pass through the UV process chamber, the coating was mostly cured but still could be scuffed off the film. After the second pass through the UV process chamber, the coating was cured and could not be scuffed off with finger pressure.

Cured release liners were prepared by coating the coating solution of Example 1 on the primed sides of 50 micrometers thick 3SAB PET films and UV-curing the coatings essentially as described above. The release liners were then aged for 5 days at a relative humidity of 50 percent at 23° C. and 70° C., respectively. The aged release and subsequent adhesion values for the release liners were then determined by carrying out the above-described test method. The resulting data is shown in Table 2 below.

TABLE 2

| Release Liner Example No. | Laminating Tape | Release (N/dm) (23° C.) | Release (N/dm) (70° C.) | Subsequent Adhesion (N/dm) (23° C.) | Subsequent Adhesion (N/dm) (70° C.) |
| --- | --- | --- | --- | --- | --- |
| 1 | Tape I | 0.17 | 0.56 | 36.79 | 23.83 |
| 1 | Tape II | 0.26 | 0.57 | 38.62 | 31.60 |

The referenced descriptions contained in the patents, patent documents, and publications cited herein are incorporated by reference in their entirety as if each were individually incorporated. Various unforeseeable modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only, with the scope of the invention intended to be limited only by the claims set forth herein as follows.

We claim:

1. A curable composition comprising
   (a) at least one polydiorganosiloxane, fluorinated polydiorganosiloxane, or combination thereof comprising reactive silane functionality comprising at least two hydroxysilyl moieties;
   (b) at least one polydiorganosiloxane, fluorinated polydiorganosiloxane, or combination thereof comprising reactive silane functionality comprising at least two hydrosilyl moieties; and
   (c) at least one photoactivatable component that, upon exposure to radiation, generates at least one base selected from phosphazenes, proazaphosphatranes, and combinations thereof;

wherein at least one of said components (a) and (b) has an average reactive silane functionality of at least three.

2. The composition of claim 1, wherein said components (a) and (b) each comprise at least one polydiorganosiloxane; wherein said polydiorganosiloxane comprises polydimethylsiloxane; and/or wherein said component (a) is hydroxyl-endblocked.

3. The composition of claim 1, wherein said component (a) is selected from polysiloxanes that are represented by the following general formula:

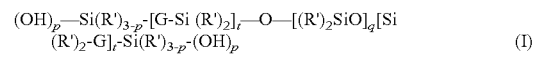

wherein each p is independently an integer of 1, 2, or 3; each G is independently a divalent linking group; each R' is independently selected from alkyl, alkenyl, fluoroalkyl, aryl, fluoroaryl, cycloalkyl, fluorocycloalkyl, heteroalkyl, heterofluoroalkyl, heteroaryl, heterofluoroaryl, heterocycloalkyl, heterofluorocycloalkyl, and combinations thereof; q is an integer of 0 to 15,000; and each t is independently an integer of 0 or 1.

4. The composition of claim 3, wherein each said G is independently selected from oxy, alkylene, arylene, heteroalkylene, heteroarylene, cycloalkylene, heterocycloalkylene, and combinations thereof; each said R' is independently selected from alkyl, fluoroalkyl, aryl, and combinations thereof; said q is an integer of 20 to 15,000; and/or said t is an integer of 0.

5. The composition of claim 1, wherein said component (a) comprises a mixture of (1) at least one polydiorganosiloxane, fluorinated polydiorganosiloxane, or combination thereof having a weight average molecular weight in the range of 300,000 to 1,000,000 and (2) at least one polydiorganosiloxane, fluorinated polydiorganosiloxane, or combination thereof having a weight average molecular weight in the range of about 150 to about 150,000; and/or wherein said component (b) has an average reactive silane functionality of at least three.

6. The composition of claim 1, wherein said component (b) is selected from polysiloxanes that are represented by the following general formula:

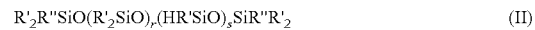

wherein each R' is independently selected from alkyl, alkenyl, fluoroalkyl, aryl, fluoroaryl, cycloalkyl, fluorocycloalkyl, heteroalkyl, heterofluoroalkyl, heteroaryl, heterofluoroaryl, heterocycloalkyl, heterofluorocycloalkyl, and combinations thereof; each R" is independently hydrogen or R'; r is an integer of 0 to 150; and s is an integer of 2 to 150.

7. The composition of claim 6, wherein each said R' is independently selected from alkyl, fluoroalkyl, aryl, and combinations thereof.

8. The composition of claim 6, wherein said R' and said R" are methyl; said r is an integer of 0; and/or said s is an integer of 40.

9. The composition of claim 1, wherein said photoactivatable component further comprises at least one photosensitizer.

10. The composition of claim 1, wherein said composition is an organometallic catalyst-free composition; wherein said composition is solventless; and/or wherein said composition has been cured.

11. A coating process comprising
(a) providing the curable polysiloxane composition of claim 1;
(b) providing at least one substrate having at least one major surface;
(c) applying said curable polysiloxane composition to at least a portion of at least one said major surface of said substrate; and
(d) inducing said curable polysiloxane composition to cure to form a coating by exposing at least a portion of said curable polysiloxane composition to radiation.

12. An article comprising at least one substrate having at least one major surface, said substrate bearing, on at least a portion of at least one said major surface, a coating prepared by the coating process of claim 11.

13. The article of claim 12, wherein said article further comprises a layer of pressure-sensitive adhesive prepared by application of a photopolymerizable composition to said coating, followed by irradiation of said photopolymerizable composition to effect photopolymerization thereof.

14. The composition of claim 1, wherein said base is selected from
(1) phosphazene compounds that are represented by the following general formula:

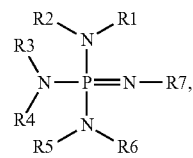

(V)

(2) proazaphosphatrane compounds that are represented by the following general formula:

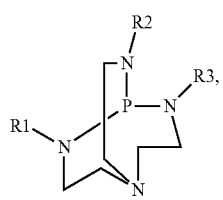

(VI)

and combinations thereof;

wherein R1, R2, R3, R4, R5, R6, and R7 are each independently selected from hydrogen, monovalent organic groups, monovalent heteroorganic groups, and combinations thereof; and
wherein any two or more of R1, R2, R3, R4, R5, R6, and R7 of said phosphazene compounds optionally can be bonded together to form a ring structure.

15. The composition of claim 1, wherein said base is selected from phosphazenes and combinations thereof.

16. The composition of claim 15, wherein said base is selected from 2-tert-butylimino-2-diethylamino-1,3-dimethylperhydro-1,3,2-diazaphosphorine, phosphazene base $P_1$-t-Bu-tris(tetramethylene), phosphazene base $P_4$-t-Bu, and combinations thereof.

17. The composition of claim 1, wherein said base is selected from proazaphosphatranes and combinations thereof.

18. The composition of claim 17, wherein said base is 2,8,9-triisopropyl-2,5,8,9-tetraaza-1-phosphabicyclo[3.3.3]undecane.

19. A curable composition comprising
(a) at least one polydiorganosiloxane, fluorinated polydiorganosiloxane, or combination thereof that is hydroxyl-endblocked;
(b) at least one polydiorganosiloxane, fluorinated polydiorganosiloxane, or combination thereof comprising at least three hydrosilyl moieties; and
(c) at least one photoactivatable component that, upon exposure to radiation, generates at least one base selected from 2-tert-butylimino-2-diethylamino-1,3-dimethylperhydro-1,3,2-diazaphosphorine, phosphazene base $P_1$-t-Bu-tris(tetramethylene), phosphazene base $P_4$-t-Bu, 2,8,9-triisopropyl-2,5,8,9-tetraaza-1-phosphabicyclo[3.3.3]undecane, and combinations thereof.

20. A curable composition comprising
(a) at least one polydiorganosiloxane, fluorinated polydiorganosiloxane, or combination thereof comprising reactive silane functionality comprising at least two hydroxysilyl moieties;
(b) at least one polydiorganosiloxane, fluorinated polydiorganosiloxane, or combination thereof comprising reactive silane functionality comprising at least two hydrosilyl moieties; and
(c) at least one photoactivatable component that, upon exposure to radiation, generates at least one base selected from 2-tert-butylimino-2-diethylamino-1,3-dimethylperhydro-1,3,2-diazaphosphorine, phosphazene base $P_1$-t-Bu-tris(tetramethylene), phosphazene base $P_4$-Bu, 2,8,9-triisopropyl-2,5,8,9-tetraaza-1-phosphabicyclo[3.3.3]undecane, and combinations thereof;
wherein at least one of said components (a) and (b) has an average reactive silane functionality of at least three.

* * * * *

UNITED STATES PATENT AND TRADEMARK OFFICE
CERTIFICATE OF CORRECTION

PATENT NO. : 8,968,869 B2  
APPLICATION NO. : 13/807344  
DATED : March 3, 2015  
INVENTOR(S) : Yu Yang et al.

Page 1 of 2

It is certified that error appears in the above-identified patent and that said Letters Patent is hereby corrected as shown below:

ON THE TITLE PAGE

First Page, Column 2 Item 56 (Other Publications)
Line 2, Delete "Organocatalyts"," and insert -- Organocatalysts", --, therefor.

IN THE SPECIFICATION

Column 9
Line 22, Delete "thereof" and insert -- thereof; --, therefor.

Column 15
Line 39, Delete "benzo[o]mate)" and insert -- benzoformate) --, therefor.

Column 16
Line 31, Delete "$NR_8$, $R_9$," and insert -- $NR_8R_9$, --, therefor.

Column 17
Line 4, Delete "stilbenzyl," and insert -- stilbenyl, --, therefor.

Column 17
Line 47, Delete "$NR_8$, $R_9$" and insert -- $NR_8R_9$ --, therefor.

Column 18
Lines 4-5, Delete "1'-diazabicyclo" and insert -- 11'-diazabicyclo --, therefor.

Column 18
Line 36, Delete "photoactivable" and insert -- photoactivatable --, therefor.

Signed and Sealed this  
Twenty-second Day of December, 2015

Michelle K. Lee  
*Director of the United States Patent and Trademark Office*

CERTIFICATE OF CORRECTION (continued)
U.S. Pat. No. 8,968,869 B2

IN THE SPECIFICATION

Column 18
Line 41, Delete "1'-diazabicyclo" and insert -- 11'-diazabicyclo --, therefor.

Column 19
Line 50, Delete "thereof" and insert -- thereof; --, therefor.

Column 25
Line 46, Delete "Aced" and insert -- Aged --, therefor.

Column 26
Line 47, Delete "diazabicylo" and insert -- diazabicyclo --, therefor.

IN THE CLAIMS

Column 30
Line 49, In Claim 20, delete "$P_4$-Bu," and insert -- $P_4$-t-Bu, --, therefor.